US010071484B2

United States Patent
Mangaser et al.

(10) Patent No.: US 10,071,484 B2
(45) Date of Patent: *Sep. 11, 2018

(54) MOBILE VIDEOCONFERENCING ROBOT SYSTEM WITH NETWORK ADAPTIVE DRIVING

(71) Applicant: INTOUCH TECHNOLOGIES, INC., Goleta, CA (US)

(72) Inventors: Amante Mangaser, Goleta, CA (US); Jonathan Southard, Santa Barbara, CA (US); Marco Pinter, Santa Barbara, CA (US); John Cody Herzog, Santa Barbara, CA (US); Charles Steve Jordan, Santa Barbara, CA (US); Yulun Wang, Goleta, CA (US); James Rosenthal, Santa Barbara, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/250,621

(22) Filed: Aug. 29, 2016

(65) Prior Publication Data
US 2016/0368146 A1 Dec. 22, 2016

Related U.S. Application Data

(63) Continuation of application No. 14/054,518, filed on Oct. 15, 2013, now Pat. No. 9,429,934, which is a
(Continued)

(51) Int. Cl.
*G05B 19/409* (2006.01)
*B25J 9/18* (2006.01)
(Continued)

(52) U.S. Cl.
CPC .......... *B25J 9/1689* (2013.01); *G05B 19/409* (2013.01); *G05D 1/0022* (2013.01);
(Continued)

(58) Field of Classification Search
CPC ........................ G05B 19/408; G05B 19/4083; G05B 19/409; G05B 1/0022; G05B 2201/0206;
(Continued)

(56) References Cited

U.S. PATENT DOCUMENTS 9,429,934 B2 * 8/2016 Mangaser ............... B25J 9/1689
2007/0199108 A1 * 8/2007 Angle ....................... B25J 5/007
318/568.12

OTHER PUBLICATIONS

Tipsuwan et al., "Gain adaptation of networked mobile robot to compensate QoS deterioration," 2002, IEEE.*

* cited by examiner

*Primary Examiner* — Spencer D Patton

(57) ABSTRACT

A remote control station that controls a robot through a network. The remote control station transmits a robot control command that includes information to move the robot. The remote control station monitors at least one network parameter and scales the robot control command as a function of the network parameter. For example, the remote control station can monitor network latency and scale the robot control command to slow down the robot with an increase in the latency of the network. Such an approach can reduce the amount of overshoot or overcorrection by a user driving the robot.

15 Claims, 6 Drawing Sheets

Related U.S. Application Data continuation of application No. 13/670,692, filed on Nov. 7, 2012, now Pat. No. 8,588,976, which is a continuation of application No. 12/561,190, filed on Sep. 16, 2009, now Pat. No. 8,340,819.

(60) Provisional application No. 61/098,156, filed on Sep. 18, 2008.

(51) Int. Cl.
*B25J 9/16* (2006.01)
*H04N 7/18* (2006.01)
*G05D 1/00* (2006.01)
*G06F 19/00* (2018.01)

(52) U.S. Cl.
CPC ......... *G06F 19/3418* (2013.01); *H04N 7/185* (2013.01); *G05B 2219/40174* (2013.01); *G05B 2219/40298* (2013.01); *G05D 2201/0206* (2013.01); *Y10S 901/01* (2013.01)

(58) Field of Classification Search
CPC .... G05B 2201/0211; G05B 2201/0207; G05B 2219/40174; G05B 2219/40406; G05B 2219/40147; G05B 2219/40151; B25J 9/1689; Y10S 901/01; Y10S 901/50
See application file for complete search history.

MOBILE VIDEOCONFERENCING ROBOT SYSTEM WITH NETWORK ADAPTIVE DRIVING

REFERENCE TO CROSS-RELATED APPLICATION

This application claims priority to Application No. 61/098,156 filed on Sep. 18, 2008.

BACKGROUND OF THE INVENTION

1. Field of the Invention

The subject matter disclosed generally relates to the field of mobile two-way teleconferencing.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

There has been marketed a mobile robot introduced by InTouch Technologies, Inc., the assignee of this application, under the trademarks COMPANION and RP-7. The InTouch robot is controlled by a user at a remote station. The remote station may be a personal computer with a joystick that allows the user to remotely control the movement of the robot. Both the robot and the remote station have cameras, monitors, speakers and microphones to allow for two-way video/audio communication. The robot camera provides video images to a screen at the remote station so that the user can view the robot's surroundings and move the robot accordingly.

The InTouch robot system typically utilizes a broadband network such as the Internet to establish the communication channel between the remote station and the robot. For various reasons the network may create an undesirable latency in the transmission of video from the robot to the remote station. When driving the robot the user primarily uses the video provided by the robot camera. Latency in the network may result in the user receiving delayed video images and cause the user to generate robot control commands that overshoot or overcorrect the movement of the robot.

BRIEF SUMMARY OF THE INVENTION

A remote control station that controls a robot through a network. The remote control station transmits a robot control command that includes information to move the robot. The remote control station monitors at least one network parameter and scales the robot control command as a function of the network parameter.

DETAILED DESCRIPTION

Disclosed is a remote control station that controls a robot through a network. The remote control station transmits a robot control command that includes information to move the robot. The remote control station monitors at least one network parameter and scales the robot control command as a function of the network parameter. For example, the remote control station can monitor network latency and scale the robot control command to slow down the robot with an increase in the latency of the network. Such an approach can reduce the amount of overshoot or overcorrection by a user driving the robot.

Figure 1:
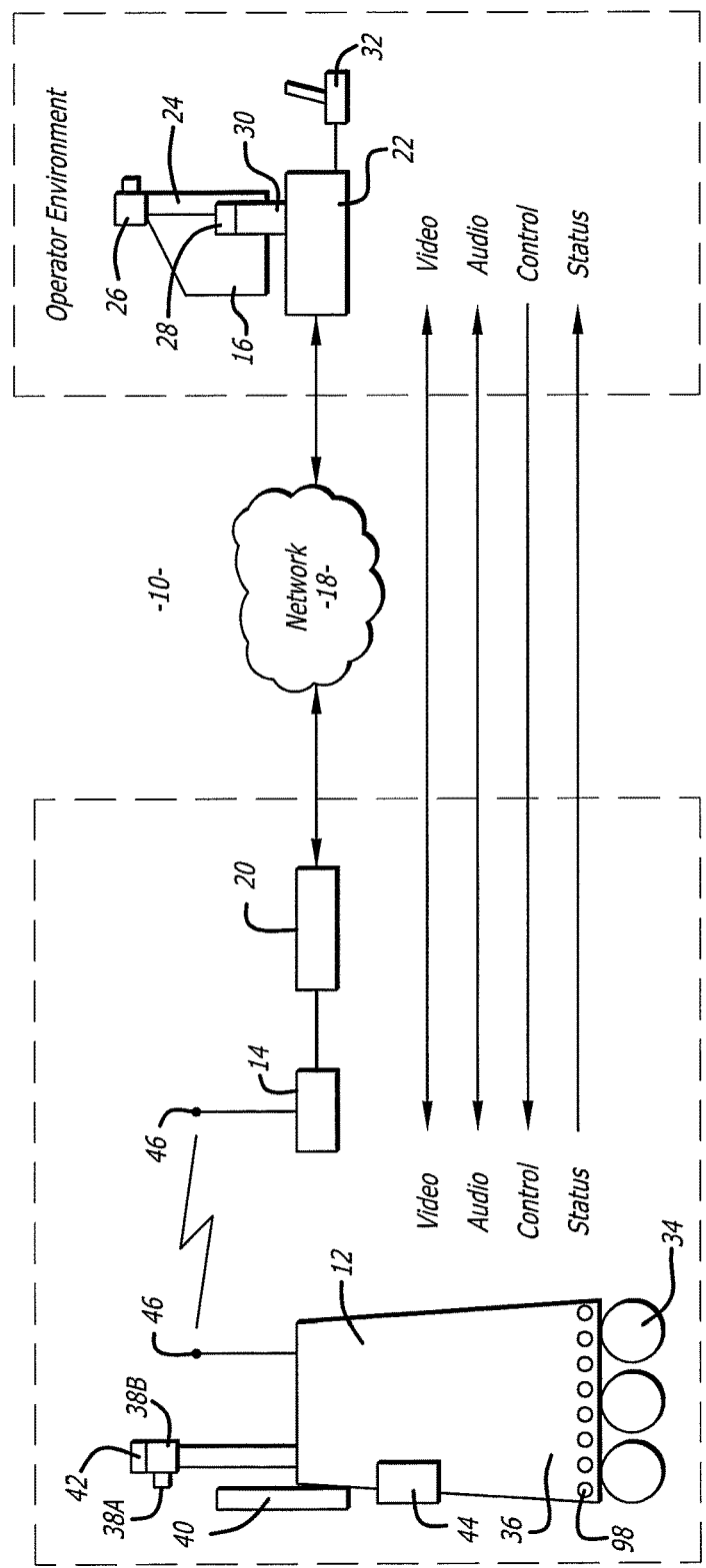
FIG. 1 is an illustration of a robotic system.

Referring to the drawings more particularly by reference numbers, FIG. 1 shows a robotic system 10 that can be used to conduct a remote visit. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. Also attached to the robot housing 36 is a pair of cameras 38, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
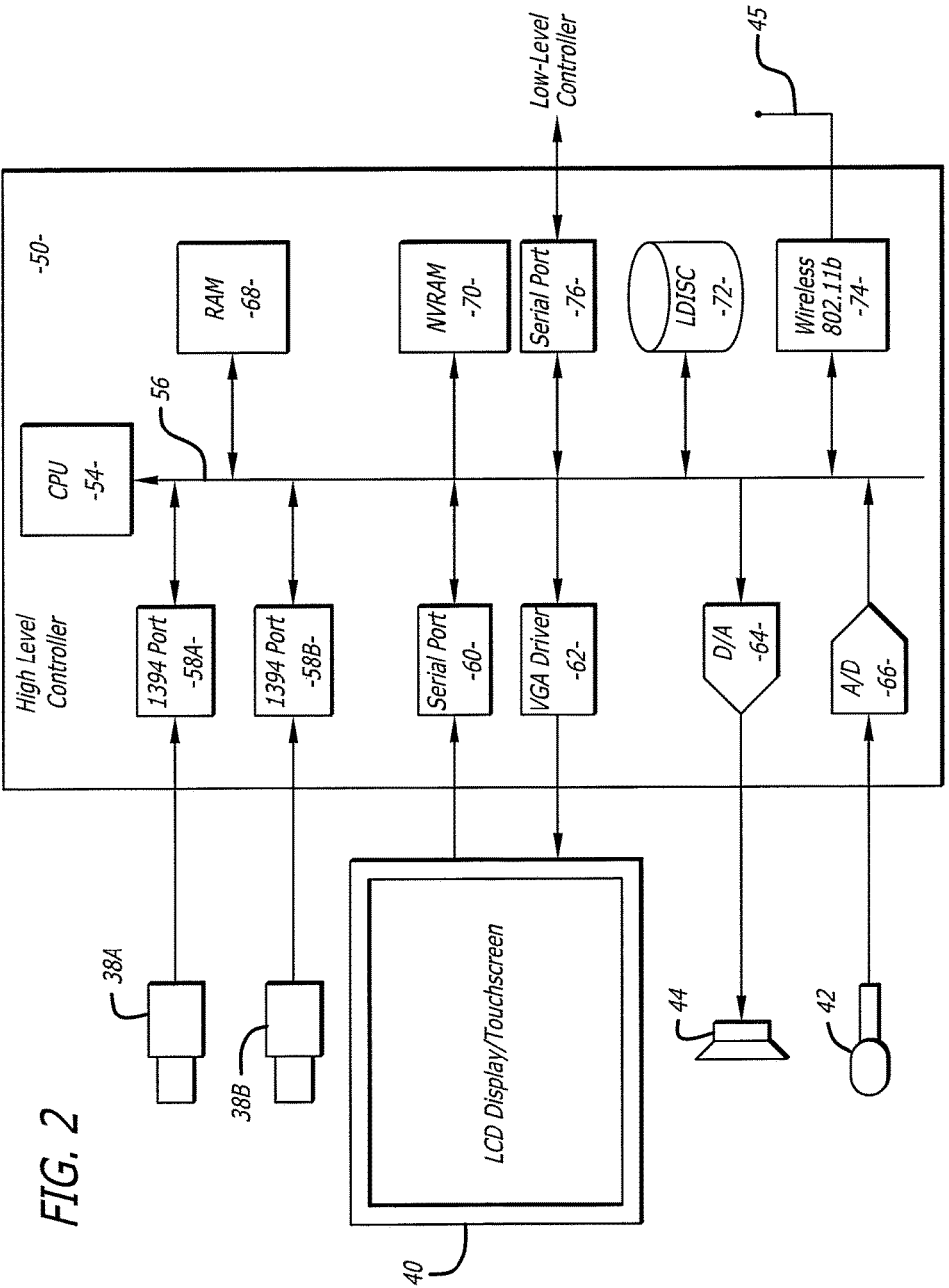
FIG. 2 is a schematic of an electrical system of a robot.
Figure 3:
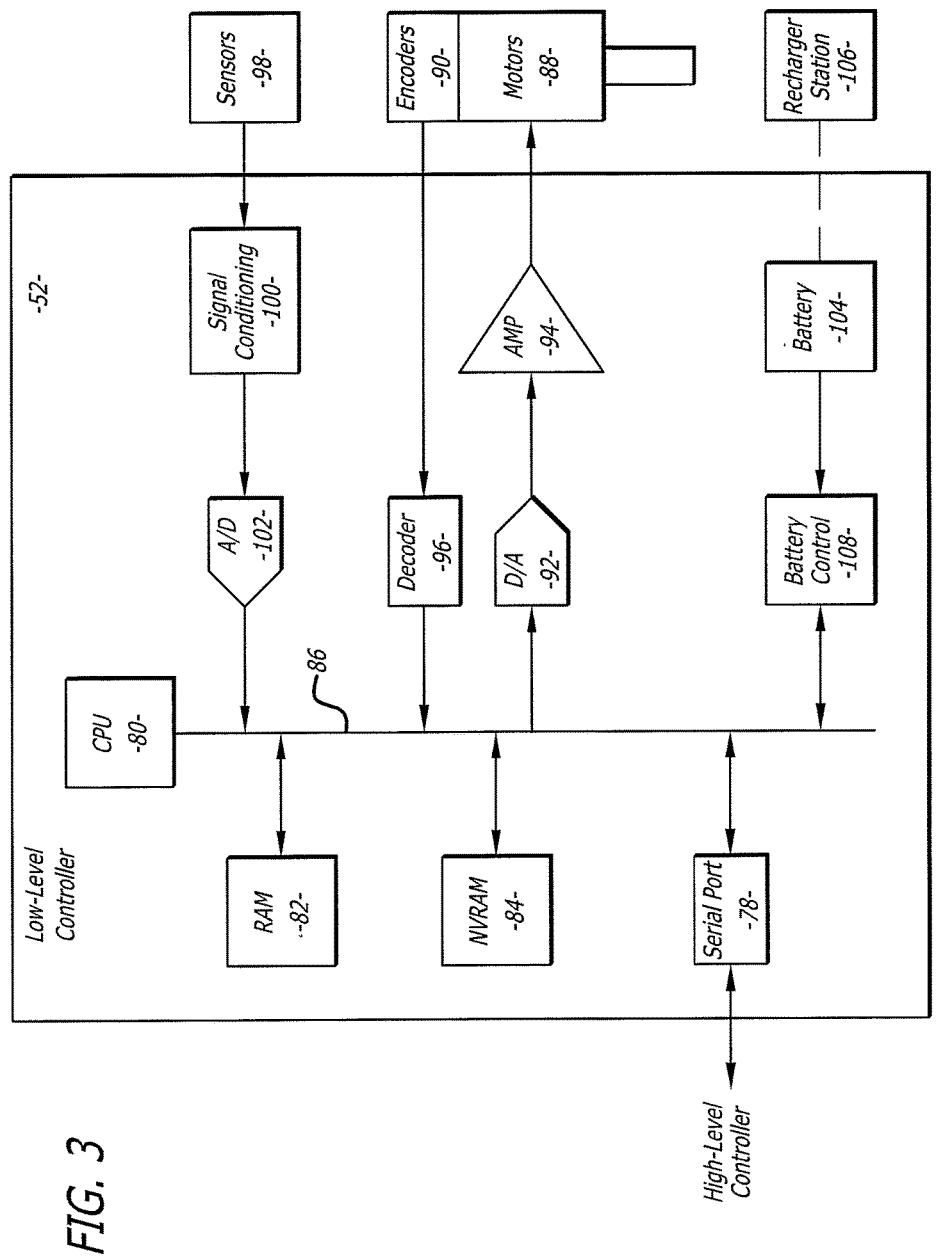
FIG. 3 is a further schematic of the electrical system of the robot.

FIGS. 2 and 3 show an embodiment of a robot 12. Each robot 12 may include a high level control system 50 and a low level control system 52. The high level control system 50 may include a processor 54 that is connected to a bus 56. The bus 56 is coupled to the camera 38 by an input/output (I/O) ports 58. The monitor 40 is coupled to the bus 56 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control communication between the robot 12 and the remote control station 16.

The remote control station 16 may include a computer that is similar to the high level controller 50. The computer would have a processor, memory, I/O, software, firmware, etc. for generating, transmitting, receiving and processing information.

The high level controller 50 may be linked to the low level controller 52 by serial ports 76 and 78. The low level controller 52 includes a processor 80 that is coupled to a RAM device 82 and non-volatile RAM device 84 by a bus 86. Each robot 12 contains a plurality of motors 88 and motor encoders 90. The motors 88 can actuate the movement platform and move other parts of the robot such as the monitor and camera. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. Each robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50.

The system may be the same or similar to a robotic system provided by the assignee InTouch-Health, Inc. of Santa Barbara, Calif. under the name RP-7. The system may also be the same or similar to the system disclosed in U.S. Pat. No. 6,925,357 issued Aug. 2, 2005, which is hereby incorporated by reference.

Figure 4:
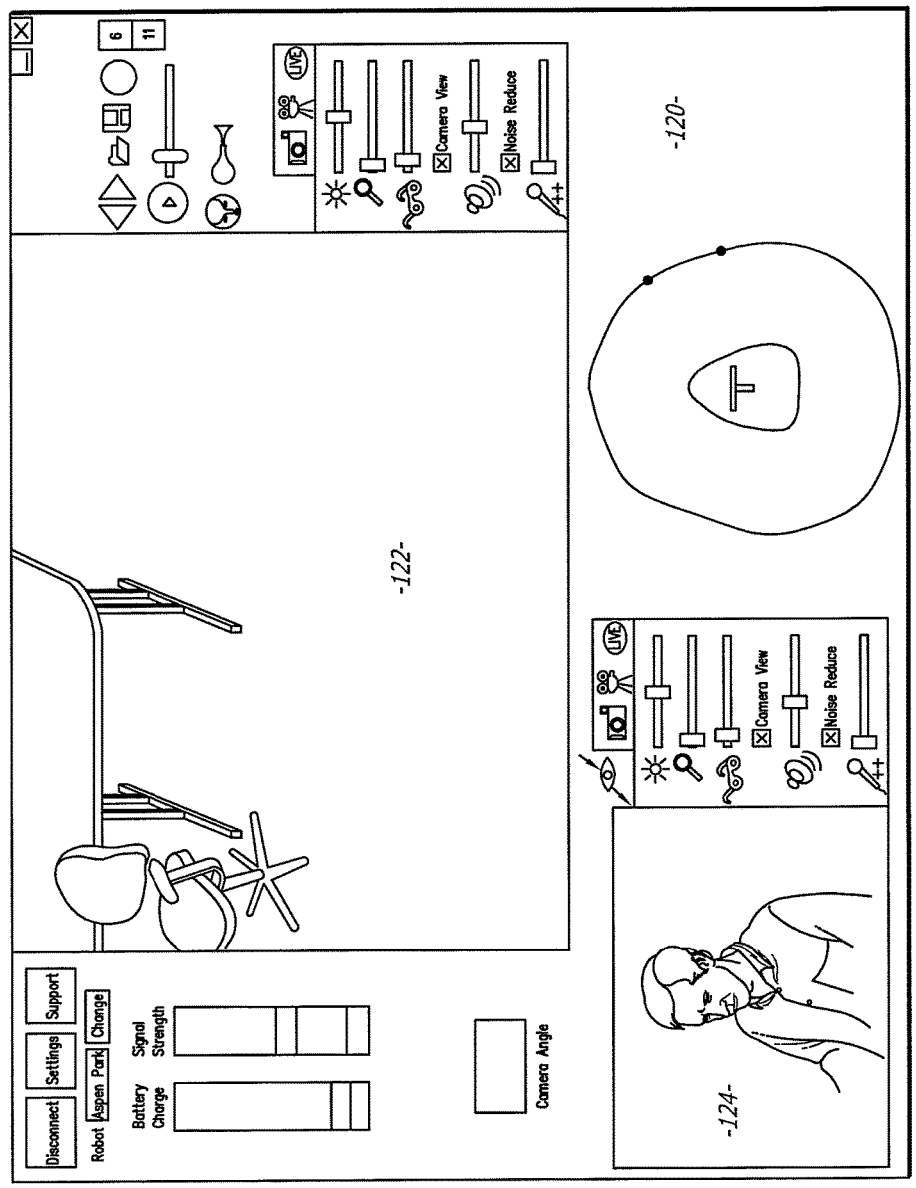
FIG. 4 is a graphical user interface of a remote station.

FIG. 4 shows a display user interface ("DUI") 120 that can be displayed at the remote station 16. The DUI 120 may include a robot view field 122 that displays a video image provided by the camera of the robot. The DUI 120 may also include a station view field 124 that displays a video image provided by the camera of the remote station 16. The DUI 120 may be part of an application program stored and operated by the computer 22 of the remote station 16.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or a facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is in use<br>Release Control | Notify requesting user that system is in use<br>No timeout<br>Put in queue or callback | Warn current user of pending user<br>Notify requesting user that system is in use<br>Set timeout = 1 m | Warn current user of pending user<br>Notify requesting user that system is in use<br>Set timeout = 5 m<br>Queue or callback | Warn current user of pending user<br>Notify requesting user that system is in use<br>No timeout<br>Callback |
| | Service | Warn current user of pending user<br>Notify requesting user that system is in use<br>No timeout | Notify requesting user that system is in use<br>No timeout<br>Callback | Warn current user of request<br>Notify requesting user that system is in use<br>No timeout<br>Callback | Warn current user of pending user<br>Notify requesting user that system is in use<br>No timeout<br>Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

| Control Commands | | |
|---|---|---|
| Command | Example | Description |
| drive | drive 10.0 0.0 5.0 | The drive command directs the robot to move at the specified velocity (in cm/sec) in the (x, y) plane, and turn its facing at the specified rate (degrees/sec). |

TABLE III-continued

Control Commands

| Command | Example | Description |
| --- | --- | --- |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to saveHeadPosition overwrites any previously saved position. |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records data internally to estimate average and maximum latency over the course of a session, which it prints to log files. |

TABLE III-continued

| Control Commands | | |
|---|---|---|
| Command | Example | Description |
| userTask | userTask "Jane Doe" "Remote Visit" | The userTask command notifies the robot of the current user and task. It typically is sent once at the start of the session, although it can be sent during a session if the user and/or task change. The robot uses this information for record-keeping. |

Table IV provides a list of reporting commands that are generated by the robot and transmitted to the remote station through the network.

TABLE IV

| Reporting Commands | | |
|---|---|---|
| Command | Example | Description |
| abnormalExit | abnormalExit | This message informs the user that the robot software has crashed or otherwise exited abnormally. Te robot software catches top-level exceptions and generates this message if any such exceptions occur. |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |

TABLE IV-continued

Reporting Commands

| Command | Example | Description |
| --- | --- | --- |
| version | version 1.6 | This message identifies the software version currently running on the robot. It is sent once at the start of the session to allow the station to do any necessary backward compatibility adjustments. |

The processor 54 of the robot high level controller 50 may operate a program that determines whether the robot 12 has received a robot control command within a time interval. For example, if the robot 12 does not receive a control command within 2 seconds then the processor 54 provides instructions to the low level controller 50 to stop the robot 12. Although a software embodiment is described, it is to be understood that the control command monitoring feature could be implemented with hardware, or a combination of hardware and software. The hardware may include a timer that is reset each time a control command is received and generates, or terminates, a command or signal, to stop the robot.

The remote station computer 22 may monitor the receipt of video images provided by the robot camera. The computer 22 may generate and transmit a STOP command to the robot if the remote station does not receive or transmit an updated video image within a time interval. The STOP command causes the robot to stop. By way of example, the computer 22 may generate a STOP command if the remote control station does not receive a new video image within 2 seconds. Although a software embodiment is described, it is to be understood that the video image monitoring feature could be implemented with hardware, or a combination of hardware and software. The hardware may include a timer that is reset each time a new video image is received and generates, or terminates, a command or signal, to generate the robot STOP command.

The robot may also have internal safety failure features. For example, the robot may monitor communication between the robot controller and the robot servo used to operate the platform motors. The robot monitor may switch a relay to terminate power to the platform motors if the monitor detects a lack of communication between the robot controller and the motor servo.

The remote station may also have a safety feature for the input device 32. For example, if there is no input from the joystick for a certain time interval (eg. 10 seconds) the computer 22 may not relay subsequent input unless the user presses a button for another time interval (eg. 2 seconds), which reactivates the input device.

Figure 5:
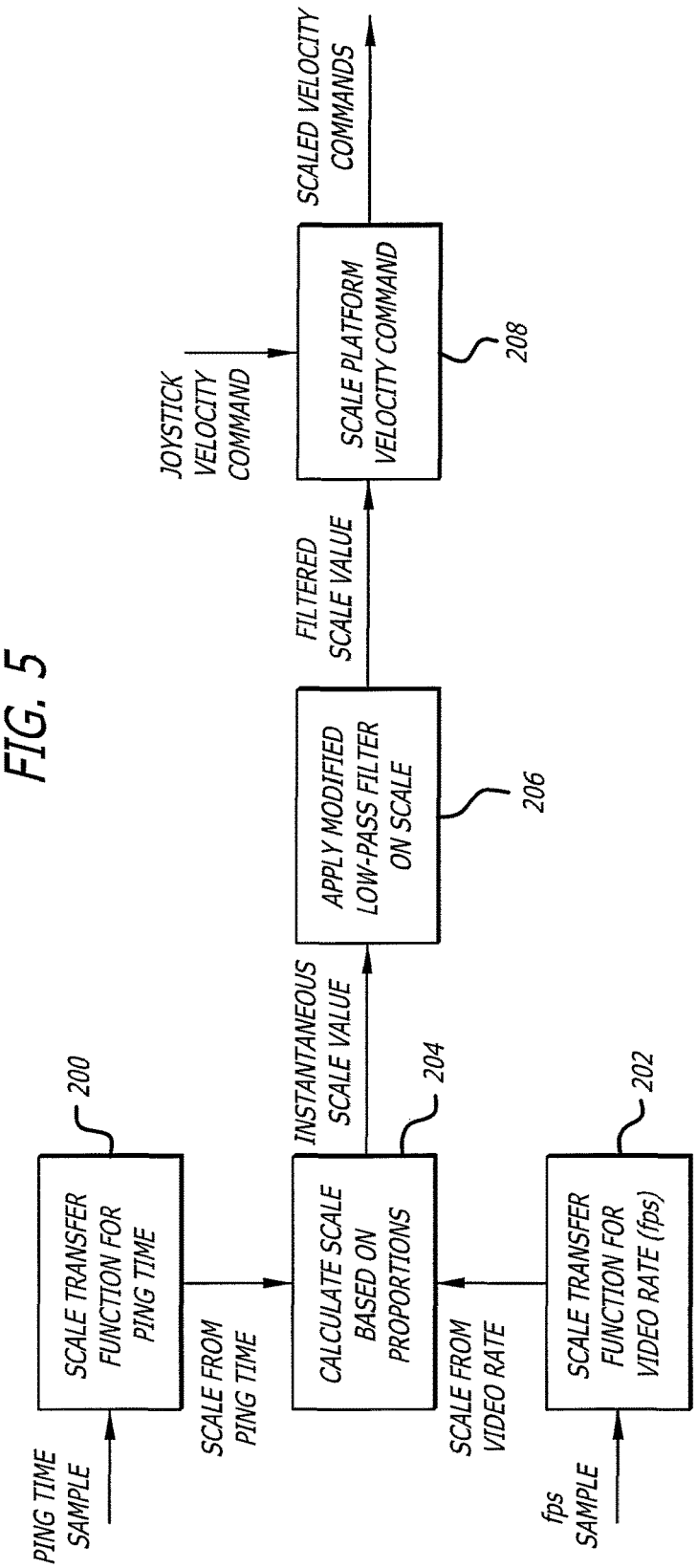
FIG. 5 is an illustration showing a process for scaling a robot control command.

The system may also scale one or more robot control commands based on a network parameter. By way of example, the remote control station may scale the velocity component of the "drive" command before transmission to the robot. FIG. 5 shows a process for scaling a robot control command. In block 200 the station may determine a scale transfer function based on a ping time. A ping time is the amount of time between when a test sample is sent from the remote station to the robot, to when the station receives the sample from the robot. In block 202 the station may determine a scale transfer function based on a video rate. The video rate is the rate at which the station receives frames of video from the robot camera.

The scale can be calculated in block 204. The scale y can be determined in accordance with the following linear piece wise functions.

$y = Y_1$ for $x \leq X_{cutIn}$ $y = Y_2$ for $x > X_{cutOff}$ $y = Y_1 + s \times (x - X_{cutOff})$ for $X_{cutIn} < x \leq X_{cutOff}$ where y is the scale, $S = (Y_1 - Y_2)(X_{cutIn} - X_{cutOff})$ x is the input variable, such as ping time or video rate; and, the capitalized entities are constant values determined by the application.

Figure 6:
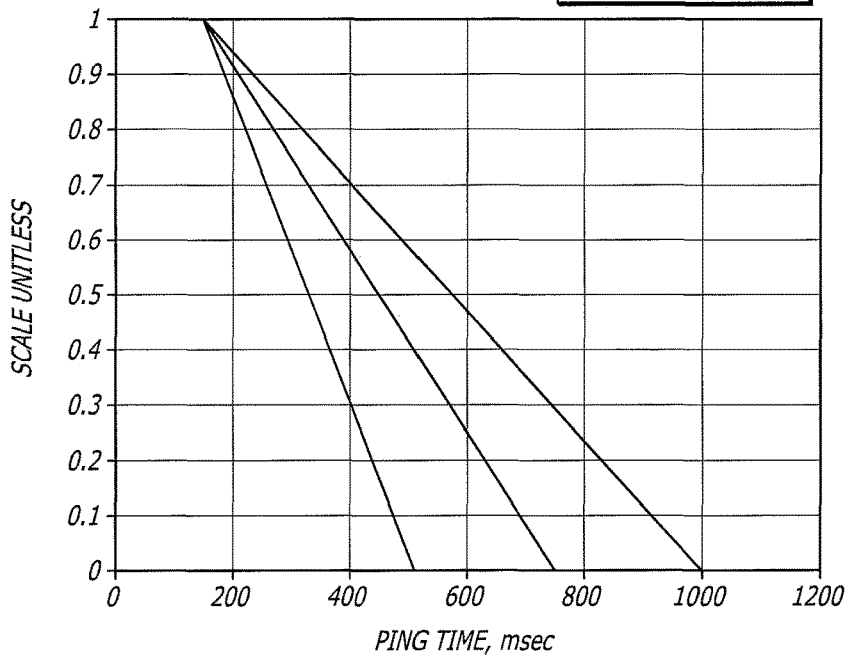
FIG. 6 is a graph showing transfer functions for scaling the robot control command based on a ping time; and, FIG. 7 is a graph showing transfer functions for scaling the robot control command based on a video rate.
Figure 7:
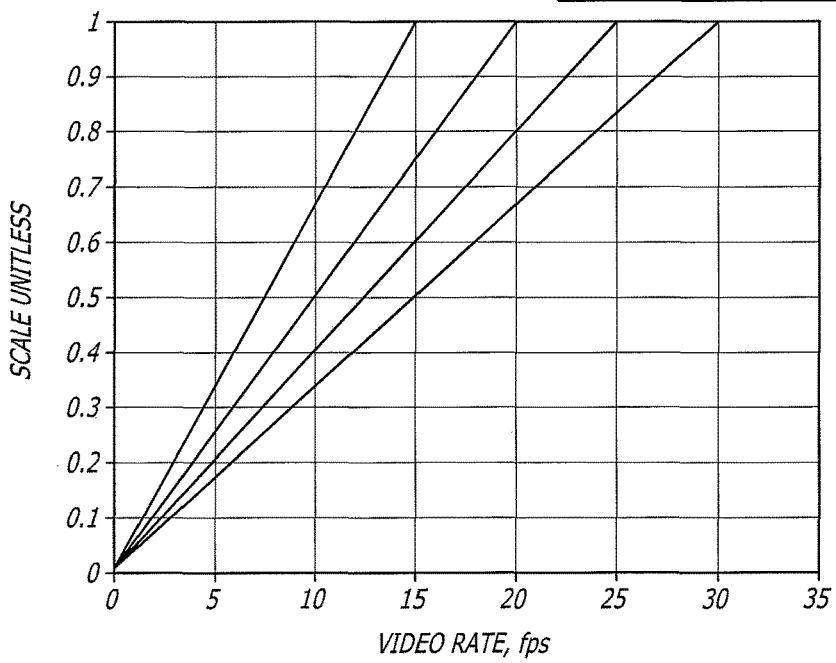

FIG. 6 is a graph that shows scale transfer functions based on ping time for a common cut-in value of 150 msec ($X_{cutIn}$) and cut-off values of 500, 750 and 1000 msec ($X_{cutOff}$). FIG. 7 is a graph that shows scale transfer functions based on video rates for a common cut-in value of 0 fps and cut-off values of 15, 20, 25 and 30 fps.

The scale can be determined utilizing both the ping time and the video rate. For example, the scale can be computed with the following equation:

Combined_scale=p×Ping_time_scale+(1.0−p)×Video_rate_scale

The parameter p may have a default value of 0.5 so that the ping time and video rate have equal weight.

Referring again to FIG. 5, the calculated scale is filtered with a low pass filter in block 206. The low pass filter 206 can be defined by the following general equation:

$f_i = \alpha \times f_{in} + (1.0 - \alpha) \times f_{i-1}$ where
$f_i$ is the current output
$f_{i-1}$ is the previous output
$f_{in}$ is the current input, and
$\alpha$ is a constant that depends on the sampling period and the filter's cut-off frequency.

The robot control command can be scaled in block 208. By way of example, the velocity command can be scaled with the calculated filtered scale value. Scaling the velocity command can control robot movement in response to changes in network latency. For example, the system can automatically slow down the robot when there is an increase in the latency of the network. This can assist in reducing overshoot or overcorrection by the user while driving the robot.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A remote controlled robot system, comprising:
 a robot that includes a camera and moves in response to a robot control command; and,
 a remote control station that includes a monitor and is coupled to said robot through a network, said remote control station transmits said robot control command that includes information to move said robot, wherein the robot control command includes a user-generated velocity command generated by the remote control station based on user input received via a user input device of the remote control station and wherein the remote controlled robot system scales said robot control command based on a monitored network parameter.

2. The system of claim 1, wherein said scaled robot control command is linearly proportional to said network parameter.

3. The system of claim 1, wherein said network parameter includes a ping time.

4. The system of claim 3, wherein said network parameter includes a video rate.

5. The system of claim 1, wherein said network parameter includes a video rate.

6. The system of claim 1, wherein said scaled robot control command is filtered with a low pass filter.

7. The system of claim 1, wherein said scaled robot command reduces a speed of said robot with an increase in a network latency.

8. The system of claim 1, wherein said robot includes a monitor, speaker and microphone and said remote control station includes a camera, speaker and microphone.

9. A method for remotely controlling a robot that has a camera, the method comprising:
displaying, on a monitor of the remote control station, an image captured by a camera of the robot;
generating, by the remote control station, a robot control command, wherein the robot control command includes a user-generated velocity command based on user input received via a user input device of the remote control station;
monitoring at least one network parameter;
scaling, by the remote control robot system, the robot control command based on the monitored network parameter; and
moving the robot in accordance with the scaled robot control command.

10. The method of claim 9, wherein the scaled robot control command is linearly proportional to the network parameter.

11. The method of claim 9, wherein the network parameter includes a ping time.

12. The method of claim 11, wherein the network parameter includes a video rate.

13. The method of claim 9, wherein the network parameter includes a video rate.

14. The method of claim 9, further comprising filtering the scaled robot control command with a low pass filter.

15. The method of claim 9, wherein the scaled robot command reduces a speed of the robot with an increase in a network latency.

* * * * *